United States Patent [19]
Weber-Unger

[11] Patent Number: 5,480,429
[45] Date of Patent: Jan. 2, 1996

[54] BREAST PROSTHESIS

[75] Inventor: Georg Weber-Unger, Kufstein, Austria

[73] Assignee: Dr. Helbig GmbH & Co Orthopädische Produkte KG, Brannenburg, Germany

[21] Appl. No.: 237,387

[22] Filed: May 3, 1994

[30] Foreign Application Priority Data

Dec. 8, 1993 [DE] Germany .................. 9318842 U

[51] Int. Cl.$^6$ .................................................. A61F 2/52
[52] U.S. Cl. ..................... 623/7; 2/267; 450/55; 450/57
[58] Field of Search ............ 450/53–57, 31–33; 2/67, 267; 623/7, 8

[56] References Cited

U.S. PATENT DOCUMENTS

| 146,805 | 1/1874 | Cox. | |
|---|---|---|---|
| 401,028 | 4/1889 | Greene. | |
| 2,611,898 | 9/1952 | Laird | 2/42 |
| 2,696,005 | 12/1954 | Schaumer | 2/267 |
| 3,020,914 | 2/1962 | Garson | 450/31 |
| 3,494,365 | 2/1970 | Beals | 623/7 |
| 4,258,442 | 3/1981 | Eberl | 623/7 |
| 4,350,162 | 9/1982 | Kearton et al. | 128/477 |

FOREIGN PATENT DOCUMENTS

| 465816 | 1/1992 | European Pat. Off. | 623/7 |
|---|---|---|---|
| 2457041 | 6/1976 | Germany | 623/7 |
| 2605148 | 8/1977 | Germany | 623/7 |
| 891088 | 12/1981 | U.S.S.R. | 623/7 |
| 94024964 | 11/1994 | WIPO | 623/7 |

Primary Examiner—David Isabella
Assistant Examiner—Laura Fossum
Attorney, Agent, or Firm—Henry M. Feiereisen

[57] ABSTRACT

A breast prosthesis to be worn in a top part of a bathing suit includes a cup-shaped prosthetic body made of soft plastic material and having a rear side which faces a wearer's body and defines a cavity. At least one stiffening rib projects radially from the rear side in a straight line and uninterrupted into the cavity between the upper rim surface and the lower rim of the prosthetic body.

10 Claims, 4 Drawing Sheets

BREAST PROSTHESIS

BACKGROUND OF THE INVENTION

The present invention refers to a breast prosthesis advantages not necessarily for use in a top part of a bathing suit, and in particular to a breast prosthesis of the type including a cup-shaped prosthetic body of soft plastic material with a rear side which faces a wearer's body and defines a cavity, and at least one stiffening rib radially extending from the surface of the cavity.

U.S. Pat. No. 4,258,442 discloses a breast prosthesis having a plastic prosthetic body of circular base area and three stiffening ribs which radially project from the rear side of the prosthetic body at an equal angular distance of 120°. The stiffening ribs extend from the outer perimeter of the prosthetic body and terminate at a radial distance before the center of the cavity which thus forms a single chamber. Each stiffening rib has a straight back side which projects beyond the ring-shaped rim surface formed between the cavity and the front side of the prosthetic body. The use of such a prosthesis in the top part of a bathing suit or a bikini becomes inconvenient for the wearer because water which accumulates in the cavity during swimming cannot be drained quickly enough from the cavity as the radial inner ends of the stiffening ribs form a bottle neck which interfere with a drainage of water. Moreover, the gaps between the ring-shaped rim surface and the wearer's body in the area of the backsides of the stiffening ribs bearing upon the wearer's body are too small to permit a rapid drainage of water from the cavity. Also, only those gaps formed in the lower area during wearing of the prosthesis are effective for draining water which flows out of the cavity through gravity. Since the backside of each stiffening rib projects beyond the rim surface of the prosthetic body, the rim surface extends almost about its entire circumference at a distance from the wearer's body. For esthetic reasons, this is undesired because the rim surface should tightly bear in particular in the upper area of the breast prosthesis upon the wearer's body.

SUMMARY OF THE INVENTION

It is an object of the present invention to provide an improved breast prosthesis advantageously but not necessarily for use in a top part of a bathing suit, obviating the aforestated drawbacks.

In particular, it is an object of the present invention to provide an improved breast prosthesis which allows a rapid drainage of accumulating water during and after swimming and a tight fit of the breast prosthesis, at least along the upper area thereof, upon the wearer's body.

These objects, and others which will become apparent hereinafter are attained in accordance with the present invention by providing the prosthetic body with at least one stiffening rib which extends in a straight line and uninterrupted between the upper rim surface and lower rim surface of the cavity when the prosthesis is worn.

The breast prosthesis according to the invention has the advantage that the stiffening rib is of a shape which enhances the flow dynamics so that the flow resistance of the rear portion of the breast prosthesis, facing the wearer's body is reduced during swimming and also allows a rapid drainage of accumulated water from the cavity when leaving the water. In addition, the stiffening rib provides the breast prosthesis with a sufficient rigidity and stiffness so that the breast prosthesis retains its configuration and shape despite increased pressure exerted by the top part of the bathing suit, and thus will not be compressed by the top part of the bathing suit.

In particular in connection with larger breast prostheses, it is preferred to provide the prosthetic body with several stiffening ribs in parallel relationship to each other between the upper and lower rim surfaces of the cavity so as to impart the breast prosthesis with improved stiffness while yet maintaining the optimum flow dynamics configuration of the rear portion. Advantageously, three parallel stiffening ribs are provided, with the central stiffening rib extending coaxial with the center plane of the prosthetic body.

According to another feature of the present invention, the prosthetic body of the breast prosthesis has a base area which is symmetric to a center plane oriented perpendicular to the base area and extending parallel longitudinally in direction of the wearer's body. In order to enhance the flow dynamics of the rear portion of the breast prosthesis and to create a high stiffness of the breast prosthesis, the stiffening rib extends coaxial with the center plane.

In order to create a particular high comfort for the wearer of the breast prosthesis, the base area of the prosthetic body is configured in form of an approximate isosceles triangle with rounded corners and a convex base. Suitably, the shanks of the triangle extend at an angle of 70°–90°, preferably 80°, preferably the central stiffening rib follows the elevational center line of the triangle.

Preferably, at least one of the stiffening ribs has a back side extending axially in direction of the stiffening rib and being arched concavely in a central area of the rib. In this manner, the central longitudinal area of the rib is prevented from contacting a surgical scar. In the event, the breast prosthesis is provided with several stiffening ribs, the back side of each stiffening rib is preferably arched concavely in a central longitudinal area of the rib.

According to another feature of the present invention, the stiffening rib has a backside which extends longitudinally in direction of the rib and is concavely arched along a central section of the rib. In this manner, a contact of the central section of the stiffening rib upon the surgical scar is prevented.

Advantageously, the backside of the stiffening rib terminates at the upper end of the rib before the upper rim surface of the prosthetic body and projects at the lower end of the rib beyond the lower rim surface of the prosthetic body in direction of the wearer's body. Thus, the upper rim surface of the prosthetic body bears tightly against the wearer's body while a gap is formed at the lower rim surface of the prosthetic body between the lower rim surface and the wearer's body to allow rapid drainage of water accumulating in the cavity of the prosthesis. Preferably, the backside of the stiffening rib terminates in a central area before the upper and lateral rim surface of the prosthetic body in order to ensure that the prosthesis bears tightly along its upper and lateral rim surfaces upon the wearer's body and to form the gap between the lower rim surface of the prosthetic body and the wearer's body.

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Figure 1:
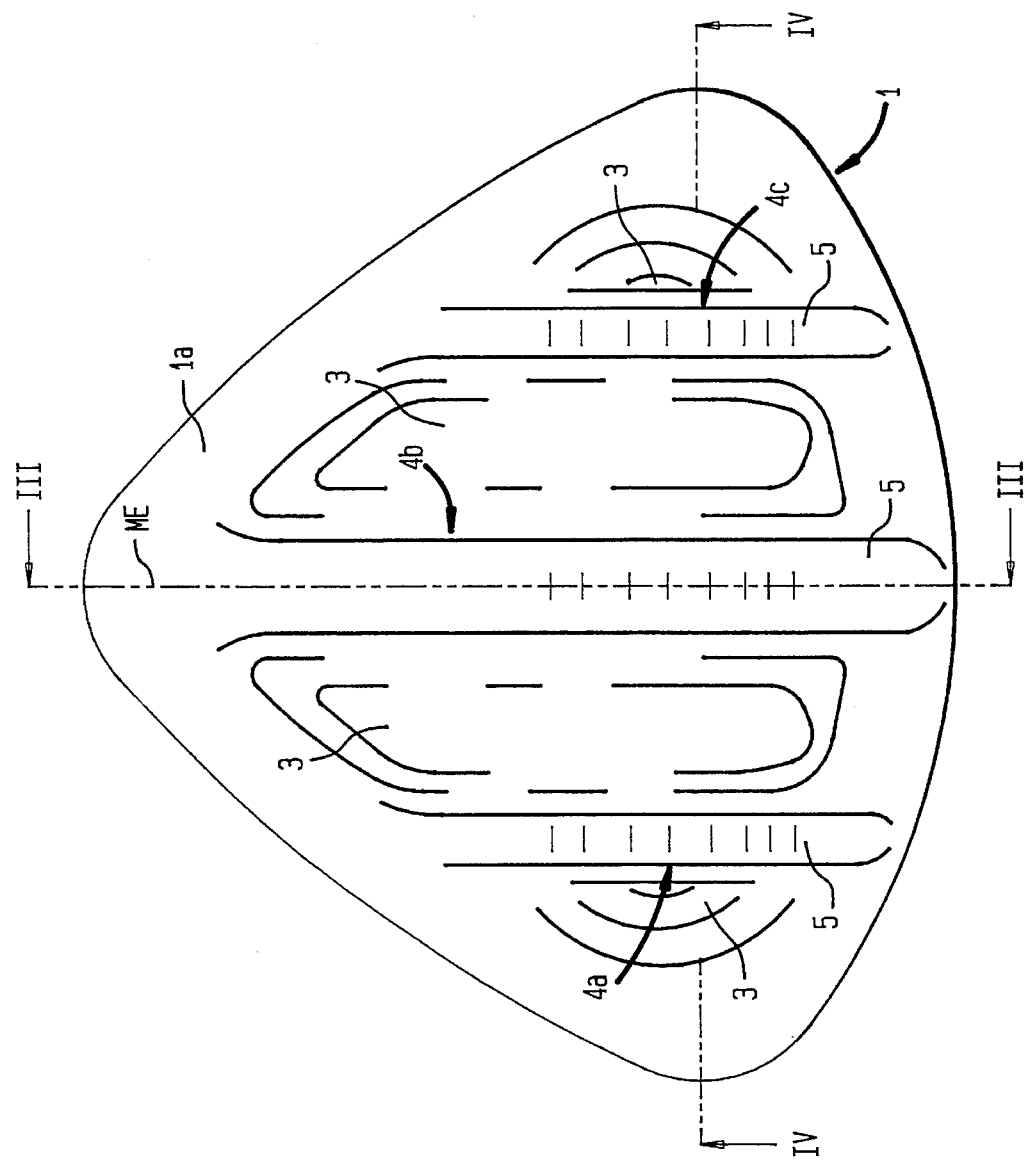
FIG. 1 is a plan rear view of a breast prosthesis according to the present invention.

Throughout all the Figures, the same or corresponding elements are always indicated by the same reference numerals.

Referring now to the drawing, and in particular to FIG. 1, there is shown a plan rear view of a breast prosthesis according to the present invention which is suitable especially to be worn in the top part of a bathing suit and is therefore called "swimming prosthesis". The breast prosthesis includes a cup-shaped prosthetic body 1 with a rear side 1a facing the wearer's body and a front side 1b. The prosthetic body 1 is made of a soft elastic plastic material such as an addition cross-linked two components silicone rubber compound which is enveloped by a polyurethane sheet. This polyurethane sheet consists of two sheet portions which respectively cover the front side 1b and rear side 1a of the prosthetic body 1 and are welded together along a rim surface 2.

Figure 2:
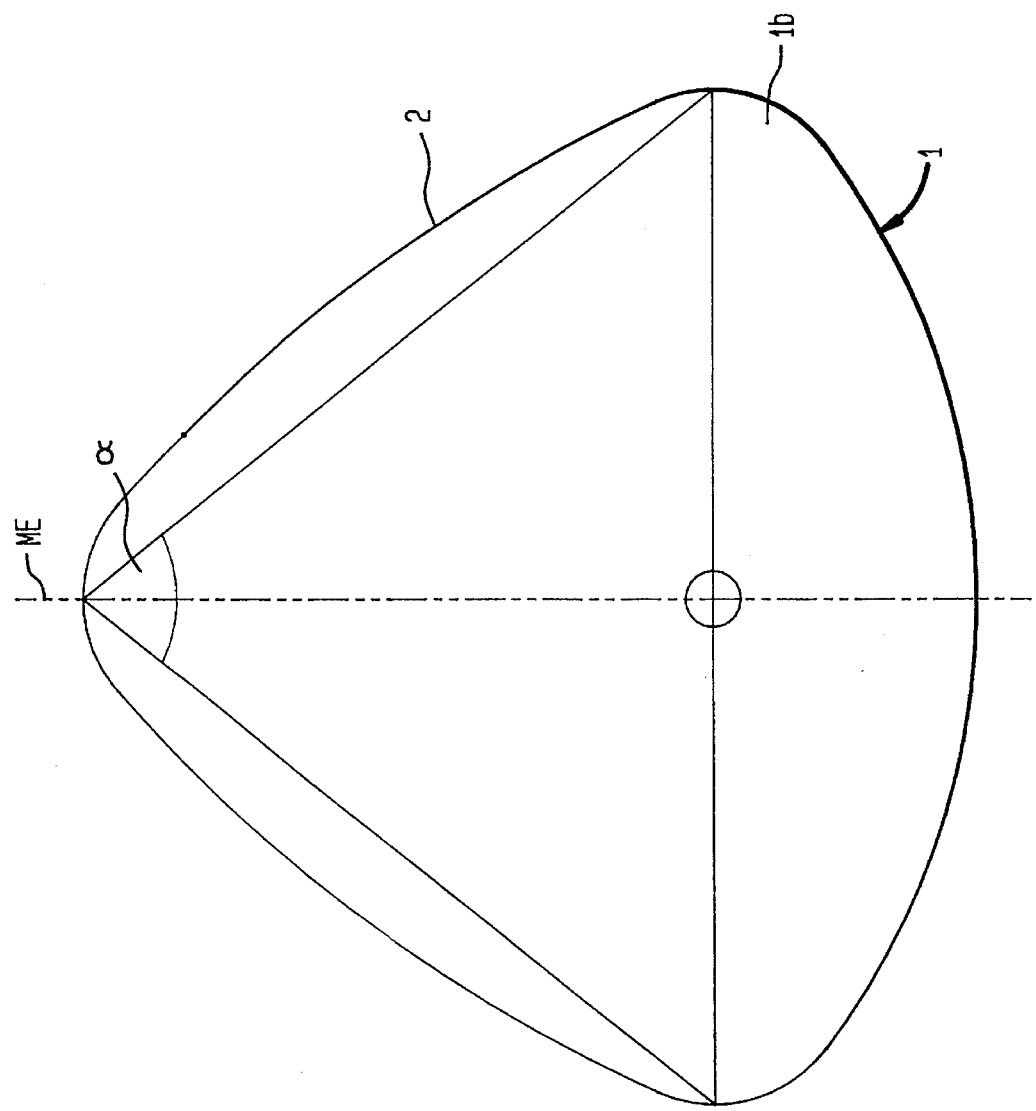
FIG. 2 is a plan front view of the breast prosthesis of FIG. 1.

FIG. 2 shows the front side 1b of the prosthetic body 1, and it can be seen that the front side 1b has a convex outer surface to follow the contour of the natural breast. The rear side 1a of the prosthetic body 1, as shown in FIG. 1, forms a cavity 3, with three parallel stiffening ribs 4a, 4b, 4c extending radially from the rear side 1a in direction of the wearer's body.

From the plane of projection as shown in FIGS. 1 and 2, is will be recognized that the prosthetic body 1 has a base area which approximates the form of an isosceles triangle with rounded corners and convex base, and with the shanks thereof extending at an angle α in the range of about 75°–90°, preferably 80°. The prosthetic body 1 is symmetric to a center plane ME which extends perpendicular to the base area of the prosthetic body 1.

The breast prosthesis is worn in the top part of a bathing suit in such a manner that the center plane ME extends parallel longitudinally in direction of the wearer's body, with the angle α positioned at the upper end of the prosthetic body 1. It will be understood that the reference to "upper" means the position at straight pasture of the wearer.

The stiffening ribs 4a, 4b, 4c extend in a straight line and continuous between the upper and lower sections of the rim surface 2 of the cavity 3, with the central stiffening rib 4b extending coaxial with the center plane ME and the two lateral stiffening ribs 4a, 4c being spaced from the central stiffening rib 4b by a same distance.

Figure 3:
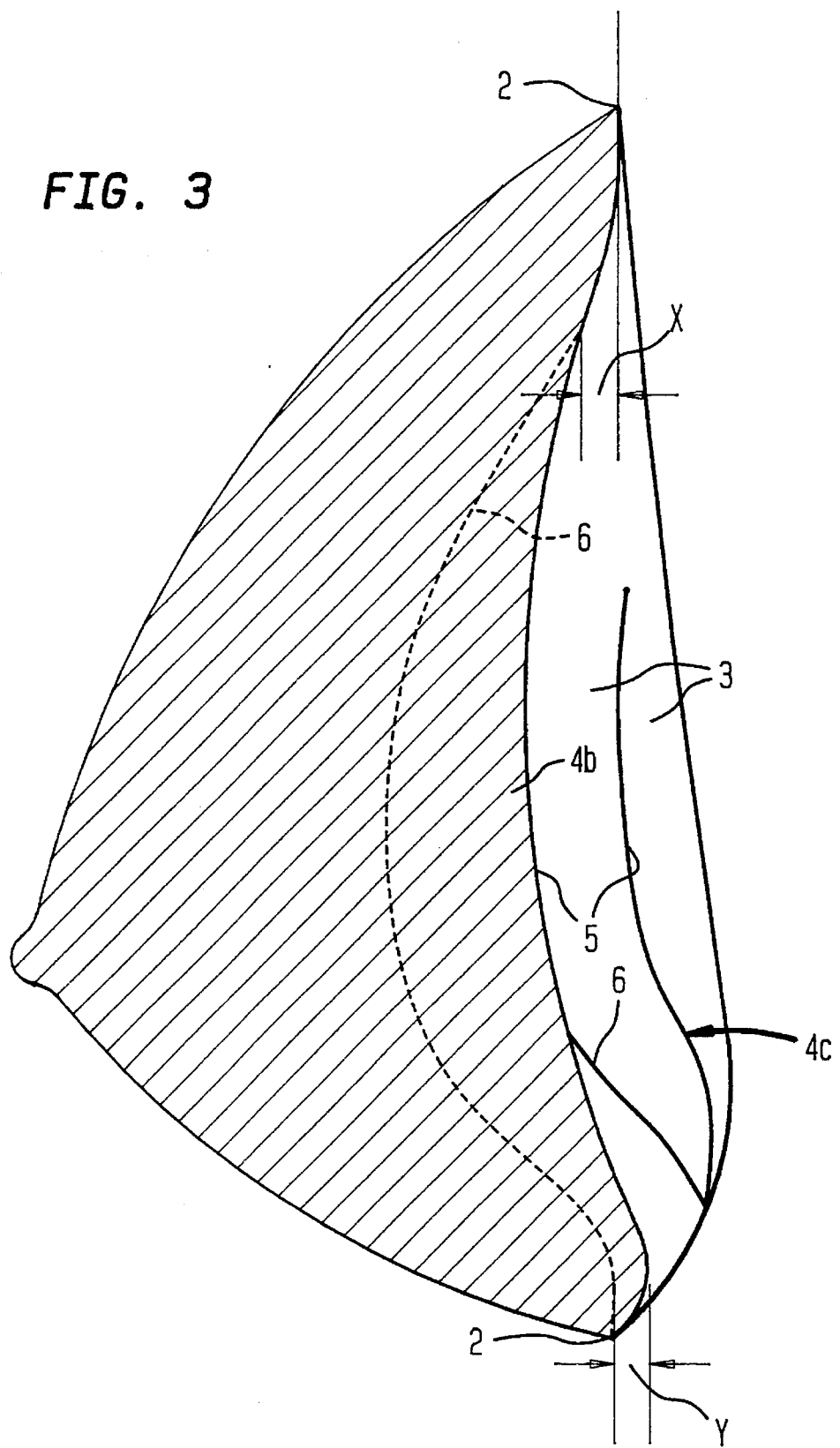
FIG. 3 is a longitudinal section of the breast prosthesis taken along the line III—III in FIG. 1.

As shown in FIG. 1, each stiffening rib 4a, 4b, 4c has a straight backside 5 which is bounded by a line measured from the highest elevation from the bottom 6 of the cavity 3. As can be seen from FIG. 4, the backside 5 of each stiffening rib 4a, 4b, 4c has a convexly arched configuration and is concavely arched longitudinally in a central area of each stiffening rib 4a, 4b, 4c, as best seen in FIG. 3. Thus, a gap is formed along the central area of each stiffening rib 4a, 4b, 4c between the backside 5 and the wearer's body.

Figure 4:
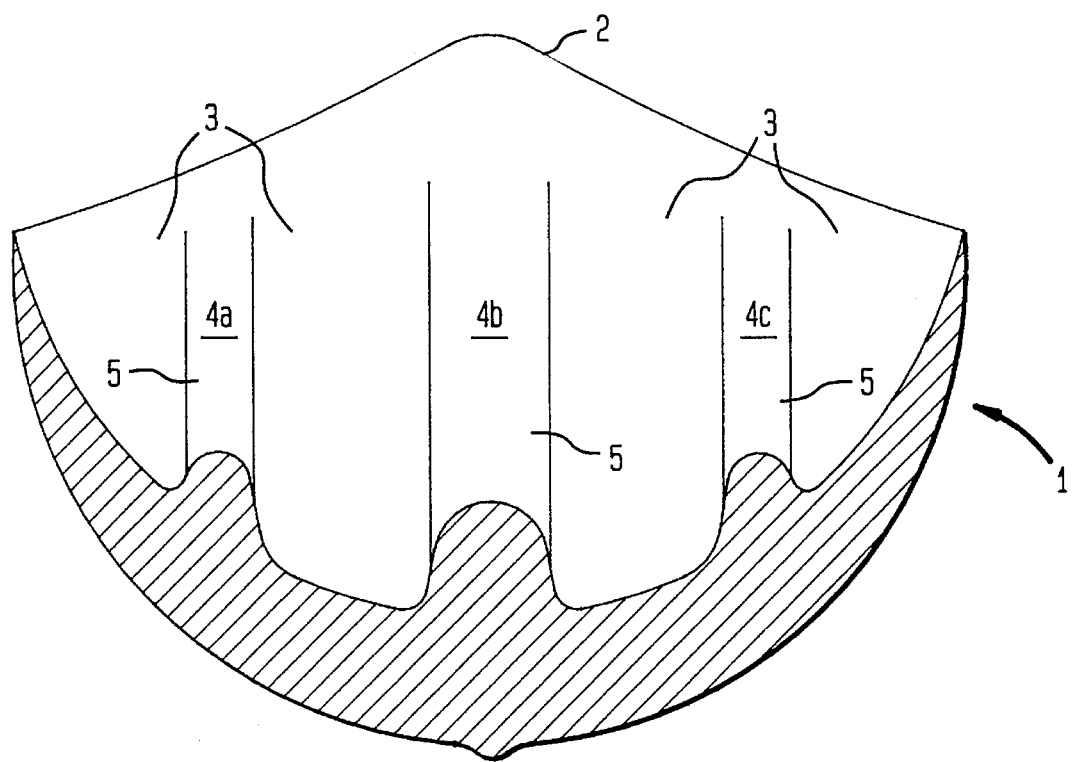
FIG. 4 is a cross sectional view of the breast prosthesis taken along the line IV—IV in FIG. 1.

As shown in particular in FIG. 4, the stiffening ribs 4a, 4b, 4c terminate before the upper section of the rim surface 2 of the prosthetic body e.g. by a distance X (FIG. 3). Also along the central area of each stiffening rib 4a, 4b, 4c, the backside 5 terminates before the upper and the lateral sections of the rim surface 2 of the prosthetic body 1. At the lower end of each stiffening rib 4a, 4b, 4c, the backside 5 projects beyond the lower rim surface 2 in direction of the wearer's body, e.g. by a distance Y, as indicated in FIG. 3. Thus, the prosthetic body 1 bears tightly upon the wearer's body with its lateral and upper sections of the rim surface 2 while the lower section of the rim surface 2 is spaced at a distance from the wearer's body to form a gap for permitting outflow of accumulated water during swimming.

While the invention has been illustrated and described as embodied in a breast prosthesis, it is not intended to be limited to the details shown since various modifications and structural changes may be made without departing in any way from the spirit of the present invention.

What is claimed as new and desired to be protected by Letters Patent is set forth in the appended claims:

1. A breast prosthesis for a woman who underwent mastectomy, comprising:

a prosthetic body of soft plastic material, said prosthetic body being configured in form of a cup with a convex front side and a concave rear surface facing a wearer's body and defining a cavity; and at least one stiffening rib providing reinforcement and stiffness such that said prosthetic body substantially retains its shape, said stiffening rib projecting from said rear surface into said cavity substantially in a straight line and continuous over an entire length from an upper perimeter to a lower perimeter, with said stiffening rib having an upper end terminating before the upper perimeter of said cavity to thereby allow the upper perimeter to sit tightly against the wearer's body.

2. The breast prosthesis defined in claim 1 wherein there is a plurality of said stiffening ribs, said stiffening ribs extending parallel between the upper perimeter and the lower perimeter of said cavity.

3. The breast prosthesis defined in claim 1 wherein said prosthetic body has a center plane, said prosthetic body is symmetrical with respect to said center plane, with said stiffening rib extending coaxial with said center plane.

4. The breast prosthesis defined in claim 3 wherein there are three of said stiffening ribs extend parallel between the upper perimeter and the lower perimeter of said cavity, with one of said stiffening ribs being arranged centrally coaxial with said center plane between the other two stiffening ribs.

5. The breast prosthesis defined in claim 3 wherein said prosthetic body is configured in a form of an approximate isosceles triangle having rounded corners, with the triangle having two sides forming at an angle of 70° to 90°, said stiffening rib extending coaxial with said center line of the triangle.

6. The breast prosthesis defined in claim 5 wherein said angle is 80°.

7. The breast prosthesis defined in claim 1 wherein each said stiffening rib has a backside extending longitudinally in a direction of said stiffening rib and being concavely arched in a central area of said stiffening rib.

8. The breast prothesis defined in claim 2 wherein each of said stiffening ribs has a backside extending longitudinally in a direction of said stiffening ribs and being concavely arched in a central area of said stiffening ribs.

9. The breast prosthesis defined in claim 1 wherein said stiffening rib has a lower end projecting from the lower perimeter of said cavity in a direction of the wearer's body to form a gap for drainage.

10. The breast prosthesis defined in claim 9 wherein said stiffening rib has a central area which is set back relative to the upper and lateral perimeter of said cavity.

\* \* \* \* \*

UNITED STATES PATENT AND TRADEMARK OFFICE
CERTIFICATE OF CORRECTION

PATENT NO. : 5,480,429
DATED      : January 2, 1996
INVENTOR(S) : Georg Weber-Unger It is certified that error appears in the above-indentified patent and that said Letters Patent is hereby corrected as shown below:

Column 1, lines 2 and 3: change "advantages not necessarily for use" to --advantageously but not necessarily for use--.

Col. 4,
Claim 4, line 39: change "extend" to --extending--.

Col. 4,
Claim 5, lines 46 and 47: change "with the triangle having two sides" to --with the triangle having a center line and being defined by two sides--.

Signed and Sealed this

Thirteenth Day of August, 1996

Attest:

BRUCE LEHMAN

*Attesting Officer*          *Commissioner of Patents and Trademarks*